United States Patent [19]

Leary

[11] Patent Number: 5,092,455
[45] Date of Patent: Mar. 3, 1992

[54] SUTURE RETAINER

[75] Inventor: Craig W. Leary, Bridgeport, Conn.

[73] Assignee: United States Surgical Corporation, Norwalk, Conn.

[21] Appl. No.: 533,461

[22] Filed: Jun. 5, 1990

[51] Int. Cl.⁵ .............................................. A61B 17/06
[52] U.S. Cl. .................................. 206/63.3; 206/482; 206/483; 206/495
[58] Field of Search ...................... 206/339, 63.3, 380, 206/382, 383, 388, 408, 482, 483, 477, 495

[56] References Cited

U.S. PATENT DOCUMENTS

| | | | |
|---|---|---|---|
| 2,938,624 | 5/1960 | Runkel et al. | 206/63.3 |
| 3,206,018 | 9/1965 | Lewis et al. | 206/63.3 |
| 3,627,120 | 12/1971 | Bordeau | 206/63.3 X |
| 3,779,375 | 12/1973 | Foster | 206/63.3 |
| 3,985,227 | 10/1976 | Thyen et al. | 206/63.3 |
| 4,183,431 | 1/1980 | Schmidt et al. | 206/63.3 |
| 4,422,552 | 12/1983 | Palmer et al. | 206/482 X |
| 4,424,898 | 1/1984 | Thyen et al. | 206/63.3 |
| 4,574,948 | 3/1986 | Huck et al. | 206/63.3 |
| 4,700,833 | 10/1987 | Smith | 206/380 |

Primary Examiner—Paul T. Sewell
Assistant Examiner—Jacob K. Ackun, Jr.
Attorney, Agent, or Firm—Thomas R. Bremer; Peter G. Dilworth; Rocco S. Barrese

[57] ABSTRACT

A suture retainer is provided with an arrangement of suture-retaining tabs of complex configuration and needle-retaining tabs of a number and distribution which enable the retainer to accommodate any one of several types of combined surgical suture-needle devices.

17 Claims, 5 Drawing Sheets

SUTURE RETAINER

BACKGROUND OF THE INVENTION

This invention relates to the packaging of surgical sutures and, in particular, to a retainer card for accommodating one or more suture products, e.g., a combined surgical suture-needle device, also commonly referred to as an "armed suture", or merely "a suture", as part of a suture package.

Retainers for surgical sutures are constructed according to the nature of the suture and its intended use. There are many sizes of sutures and many materials of construction such as cotton, silk, stainless steel, and braided wire. There are also several types of needles including those of straight and curved configuration. The ideal suture package protects the suture during shipping and handling, accommodates a variety of suture and needle constructions and affords easy removability of the suture-needle device(s) therefrom.

There exists many packaging arrangements for suture-needle devices However, for the most part, these packages have been designed to accommodate a specific suture-needle configuration. That is, the package may be designed to accommodate a long straight needle or a curved needle but not both. Many packages have been developed for use with single-armed sutures, for example, a suture having a needle at one end. Packages also exist for accommodating double armed sutures, i.e., sutures possessing needles at both ends. There are also several different types of packages containing a plurality of sutures and designed in such a way as to allow all of the sutures to be removed from the package at once or one at a time.

Illustrative of known types of suture retainers are those disclosed in U.S. Pat. Nos. 3,206,018; 4,391,365, 4,572,363 and 4,700,833. The last mentioned of these disclosures, U.S. Pat. No. 4,700,833, describes a suture retainer, or winding card, possessing a base panel and several flaps which extend from, and fold over, the base panel to cover and secure a suture or combined suture-needle device disposed thereon. A number of die-cut U-shaped tabs are arranged along the periphery of the base, the convex portion the tabs being oriented toward the edges of the panel and away from its center. By slightly displacing the tabs from the plane of the base panel, the tabs may serve to receive a coiled length of suture. The base panel also possesses a pair of opposed D-shaped apertures for receiving a pin around which a suture may be wound, e.g., in a figure eight pattern, to facilitate an alternative suture-packaging operation.

SUMMARY OF THE INVENTION

It is an object of the invention to provide a suture retainer comprising a base panel possessing a plurality of spaced-apart suture-engaging tabs of compound configuration defined thereon and a plurality of spaced-apart needle-engaging tabs defined upon the base panel, the number and distribution of the needle-engaging tabs being such as to accommodate a variety of needle sizes and/or configurations.

It is a particular object of the invention to provide a suture retainer which, in its packaged and sealed configuration, exhibits a narrower profile for a given type and quantity of sutures than that of the known type of retainers, e.g., as described in U.S. Pat. No. 4,700,833 discussed above.

It is another object of the invention to provide a suture retainer which accommodates a wide variety of sutures and/or combined suture-needle devices such that the number of retainers which must be manufactured and inventoried to meet the packaging needs of a comprehensive line of suture products is kept to a minimum.

In keeping with these and other objects of the invention, there is provided a suture retainer comprising a base panel possessing a plurality of suture-engaging spaced apart tabs of compound configuration defined thereon and a plurality of spaced-apart needle-engaging tabs defined upon the base panel, said tabs being of sufficient number and distribution to accommodate a plurality of needle sizes and/or configurations.

The expression "compound configuration" as applied to the suture-engaging tabs of the retainer herein shall be understood to define such a tab having at least one pair of opposed elements with one element of the pair being elevated above, and the other element of the pair being depressed below, the plane of the base panel in the packaged condition of the suture retainer.

Compared with the generally U-shaped suture-engaging tabs of the retainer described in aforementioned U.S. Pat. No. 4,700,833, the suture-engaging tabs of the retainer of this invention, due to their compound configuration, result in a narrower packaging profile.

In addition, the provision of needle-engaging tabs upon the base panel of the suture retainer herein, a feature which is lacking in the retainer of U.S. Pat. No. 4,700,388, makes it possible for the retainer of this invention to accommodate a variety of different sizes and/or shapes of surgical needles It is therefore possible to employ one or at most very few retainer configurations to meet the packaging needs of an entire line of suture products.

BRIEF DESCRIPTION OF THE DRAWINGS

Preferred embodiments of the invention are described herein below with reference to the drawings wherein.

DETAILED DESCRIPTION OF THE PREFERRED EMBODIMENT

Figure 1:
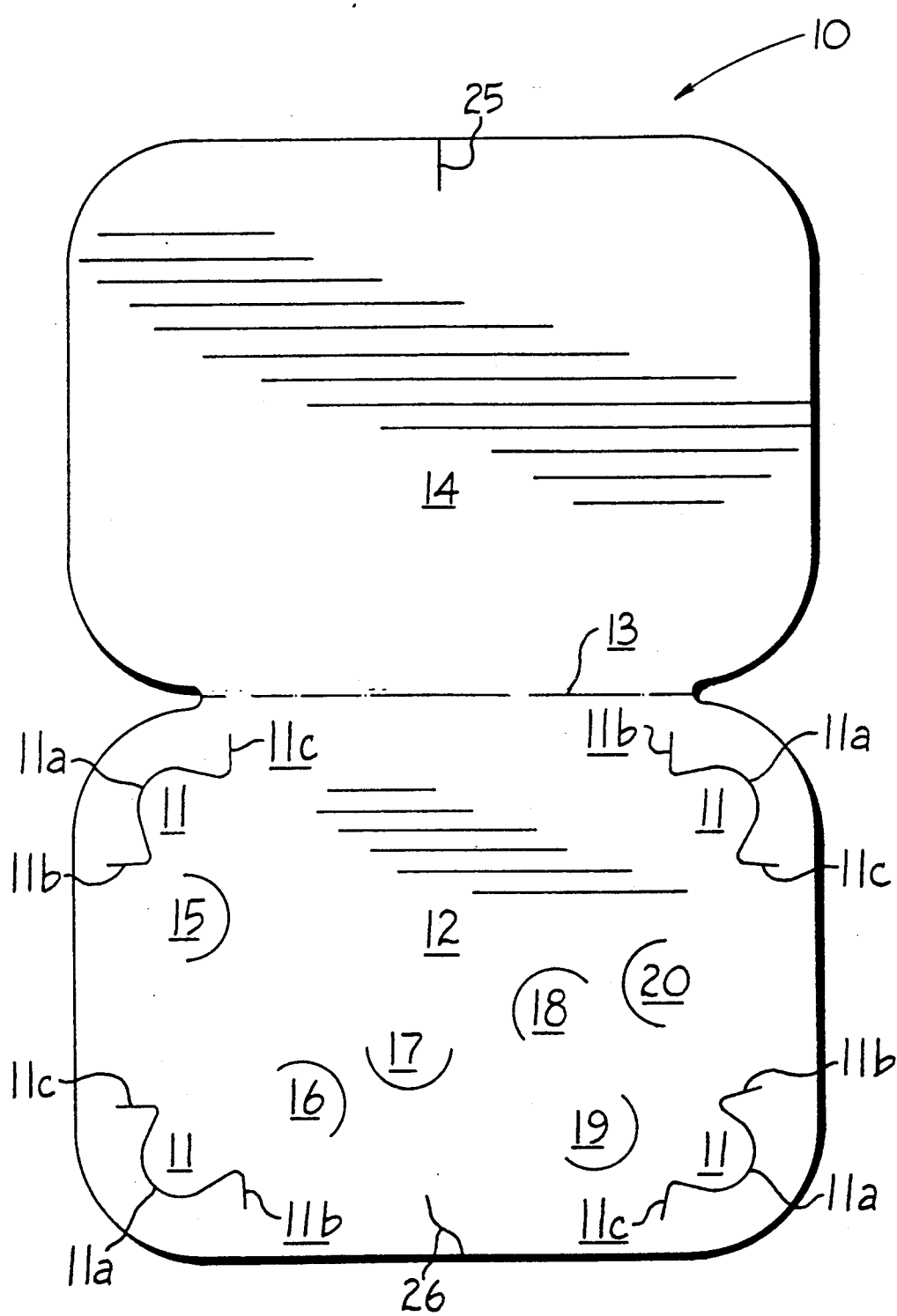
FIG. 1 is a plan view of one embodiment of a suture retainer in accordance with this invention shown in the fully open condition.

Referring initially to FIG. 1, there is illustrated a suture retainer 10 possessing a base panel 12 of rectangular square shape and an optional cover panel 14 attached to base panel 12 along common edge 13 advantageously defined by a fold line or crease which facilitates the folding over of the cover panel upon the base panel 15 in the packaged condition of the retainer.

Figure 2:
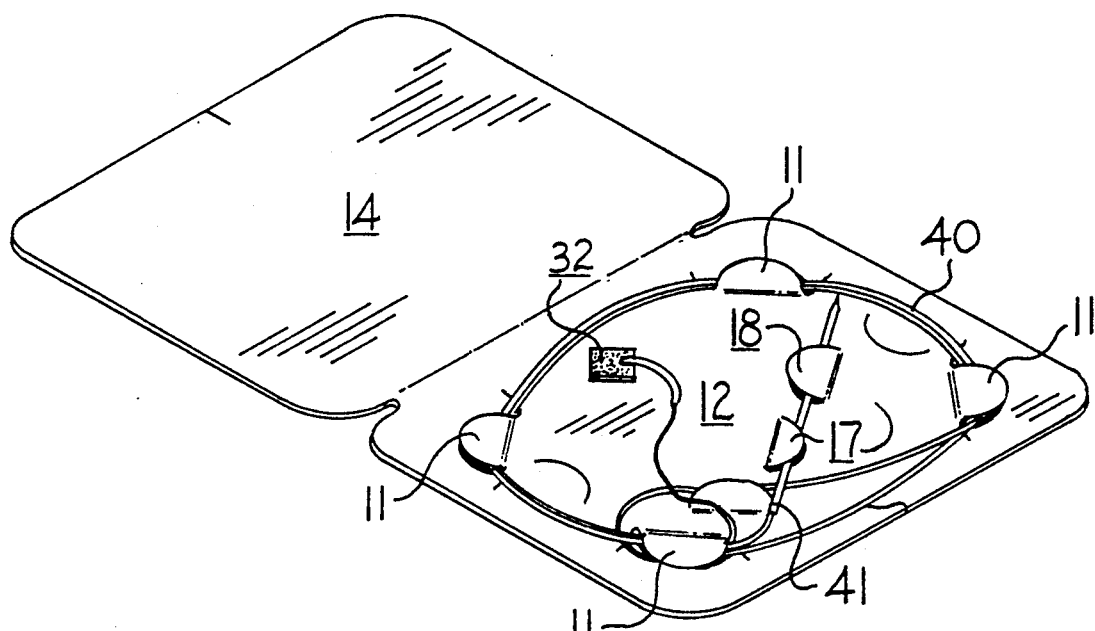
FIG. 2 is a perspective view of the suture retainer of FIG. 1 loaded with a combined surgical suture-needle device and shown in the open condition.
Figure 6:
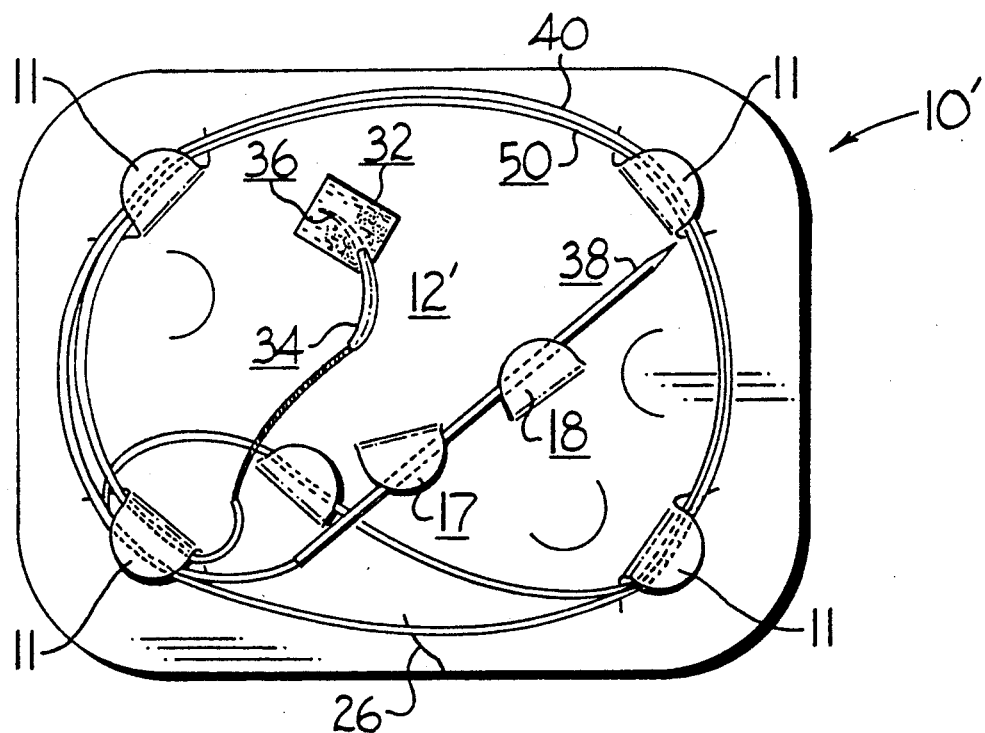
FIG. 6 is a plan view of the base panel of another embodiment of the suture retainer of FIG. 1 in accordance with this invention loaded with a double-armed suture possessing one straight needle and one small curved needle.
Figure 7:
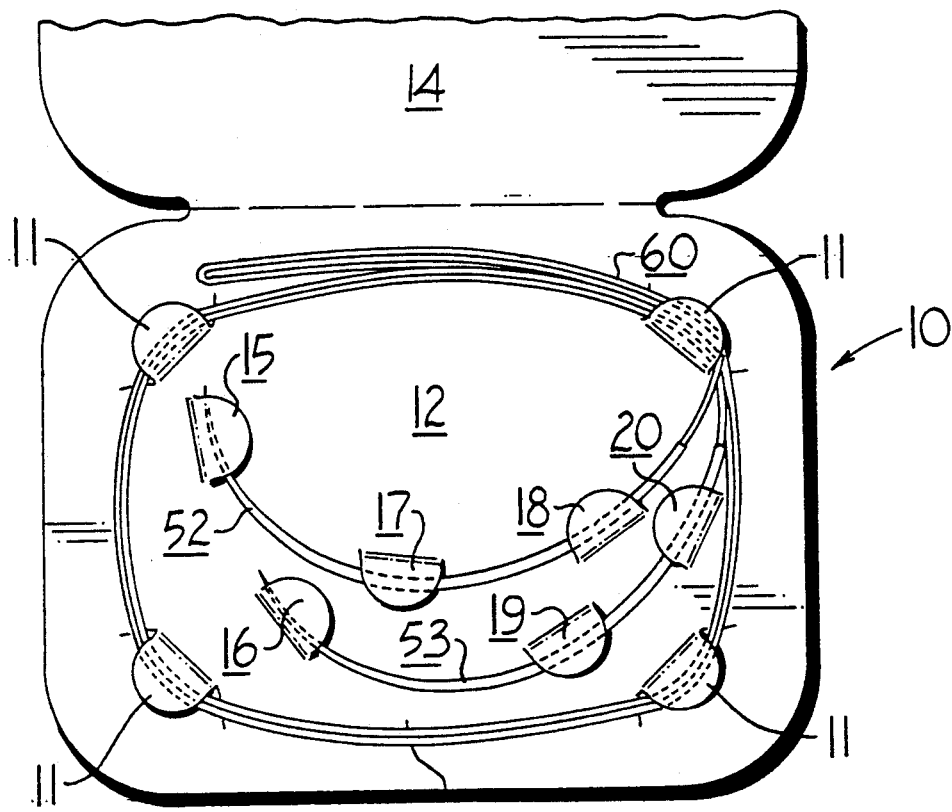
FIG. 7 is a plan view of the base panel of the suture retainer of FIG. 1 loaded with a double armed suture incorporating two curved needles.
Figure 8:
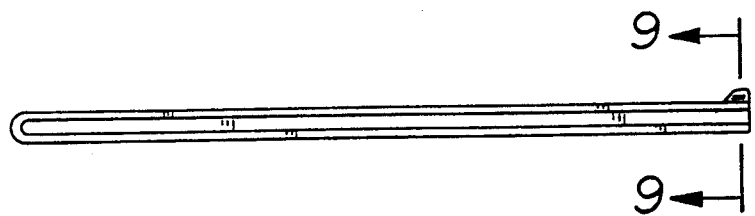
FIG. 8 is a cross sectional view of the retainer card of FIG. 3 loaded with two suture-needle assemblies.
Figure 10:
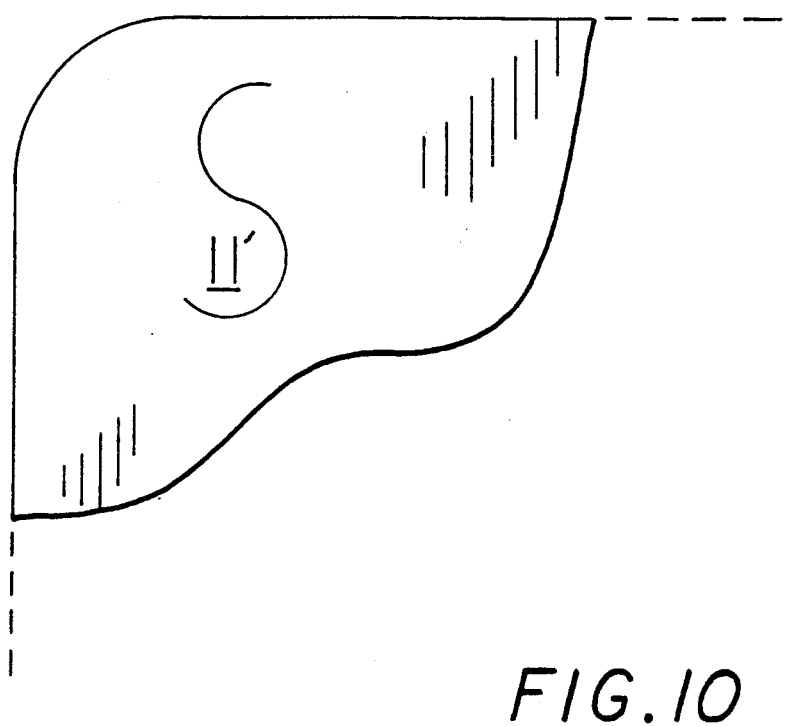
FIG. 10 is a fragmented plan view of the suture retainer of the present invention illustrating another embodiment of a suture retaining tab therewith.
Figure 11:
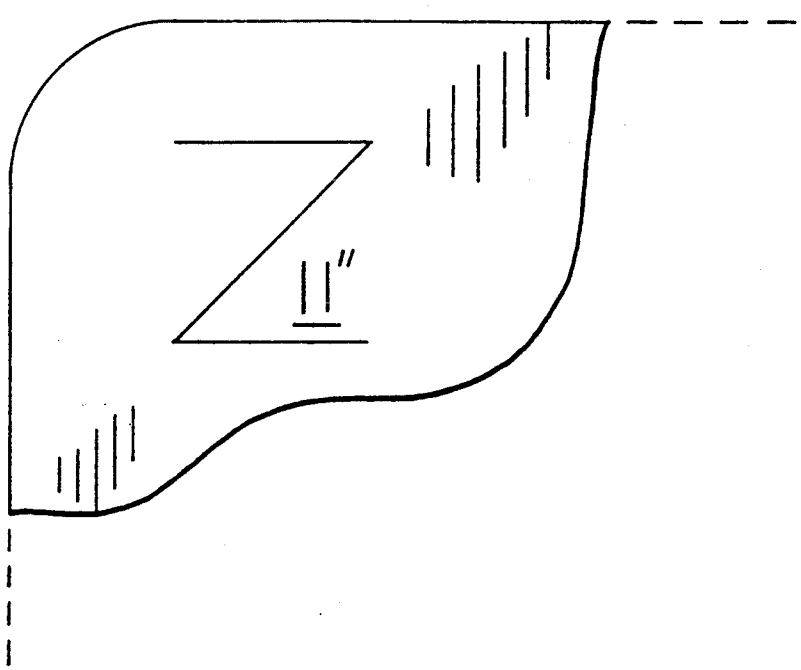
FIG. 11 is a fragmented plan view of the suture retainer of the present invention illustrating an additional embodiment of the suture retaining tab therewith.

Base panel 12 is designed to accommodate a plurality of suture/needle combinations. The sutures can be wound manually and received by the base panel in several ways. Suture retaining tabs 11 of compound configuration, e.g., the approximately W-shaped die cuts shown, are each made up of a central suture-retaining element 11a and flanking suture-retaining elements 11b and 11c oriented in a direction which is opposite that of element 11a. In the packaged condition of the suture, suture-retaining element 11a will be depressed below, or elevated above, the panel of base member 12 with flanking elements 11b and 11c being disposed outside the plane of the panel in a manner which is opposite that of element 11a. Thus, e.g., if element 11a is elevated above the plane of the panel in the packaged condition of the retainer, elements 11b and 11c will be depressed below the plane of the panel (as illustrated in FIGS. 2, 6 and 7). Suture-retaining elements 11a, 11b and 11c cooperate with other to engage the wound suture and secure it to the base panel with little if any tendency of the suture to work itself free from its engagement with these elements, a further advantage over the prior art U-shaped tab arrangement where premature disengagement of a the package suture from its retainer is more likely to occur. Tab 11 can be oriented differently from that shown; thus, e.g., the W-shape of the tab can be rotated 180° C. to orient the concave edge of element 11a toward the center of base panel 12 and away from its edge, precisely the opposite of the orientation shown. Tab 11 can be given other compound configurations in addition to the W-shape shown. Thus, e.g., tab 11 can assume the shape, or approximate shape, of an "S"(11 in FIG. 10, an "N" or a "Z"(11 in FIG. 11, etc., provided it meets the defined condition of possessing at least one pair of opposed elements with one element of the pair being elevated above, and the other element of the pair being depressed below, the plane of base panel 12 in the packaged condition of retainer 10.

The number and distribution of suture retaining tabs 11 can vary. While there must be at least two of the tabs, there can be more than the four tabs shown. The tabs can be located at the corners of base panel 12 as shown or they can be arranged differently, e.g., at the midpoint of each side of base panel 12.

C-shaped needle-retaining die-cut tabs 15-20 are strategically distributed in the central region of base panel 12, advantageously in an irregular or asymmetric pattern such as that shown to accommodate any of a variety of needle sizes and configurations.

Figure 3:
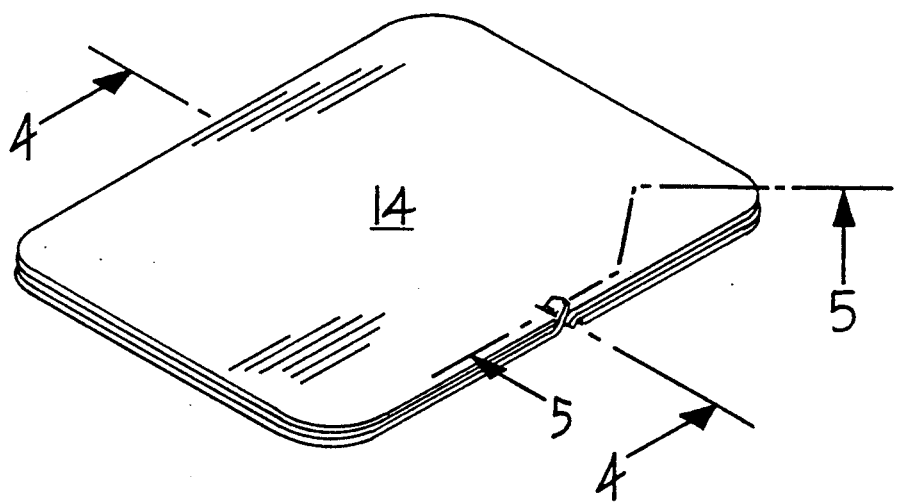
FIG. 3 is a perspective view of the loaded suture retainer of FIG. 2 shown in the fully closed and locked condition.
Figure 4:
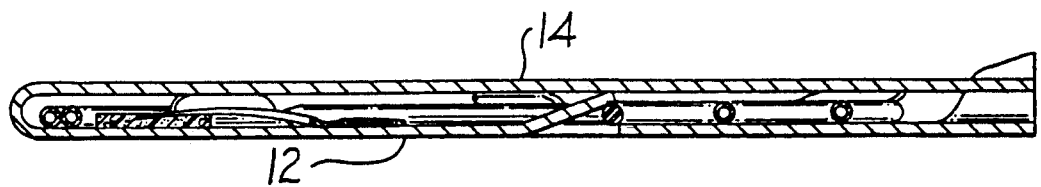
FIG. 4 is a cross sectional view of the suture retainer of FIG. 3 taken along line 4—4 thereof.
Figure 5:
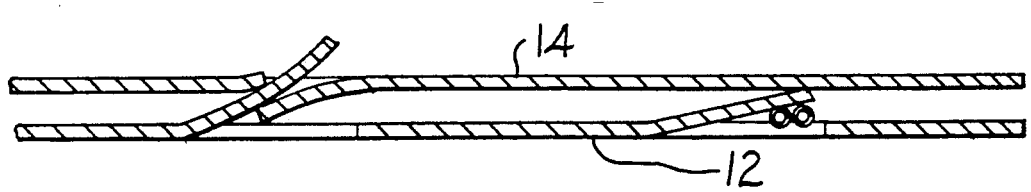
FIG. 5 is an expanded view of a sectional area of the suture retainer of FIG. 3 taken along line 5—5 thereof.
Figure 9:
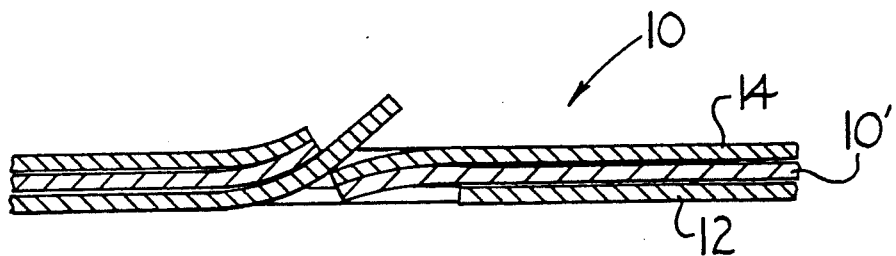
FIG. 9 is an expanded sectional view illustrating in detail the locking mechanism of the suture retainer of FIG. 3.

On folding over of cover panel 14 on base panel 12, slit 25 on cover panel 14 can be made to engage slit 26 on base panel 12 by a twisting action which locks the panels together as shown in FIG. 3. This locking engagement is illustrated in greater detail in FIGS. 4, 5 and 9. In the embodiment shown in FIG. 9, a second retainer 10' consisting solely of a base panel 12', e.g., as shown in FIG. 6, is sandwiched between base panel 12 and cover panel 14 of first retainer 10.

In the suture retainer shown in FIGS. 2, suture 40 is wound about suture-retaining tabs 11, straight needle 41 being retained by needle-retaining tabs 17 and 18. The packaging arrangement of double armed suture-needle device 50 on suture retainer 10' of FIG. 6 is similar, suture 40 being wound about tabs 11, end 32 of curved needle 34 piercing polymeric foam section 36 to safely secure this needle in place and straight needle 38 being secured in place by needle retaining tabs 17 and 18. In yet another packaging arrangement, the suture component of double armed suture 60 of retainer card 10 shown in FIG. 7 is wound about tabs 11, first curved needle 52 being retained by tabs 15, 17 and 18 and second curved needle 53 being retained by tabs 16, 19 and 20.

What is claimed is:

1. A suture retainer comprising:
   a base panel possessing a plurality of spaced-apart suture-engaging tabs defined thereon,
   each said suture-engaging tab comprising at least one pair of opposing elements, with one element of said pair being elevated above a plane of said base panel and said other element of said pair being depressed below said base panel plane, when said suture retainer is in packaged condition,
   a plurality of spaced-apart needle-engaging tabs defined upon the base panel,
   the number and distribution of the needle-engaging tabs being such as to accommodate a variety of needle sizes or configurations, and
   at least one closure panel joined to the base panel.

2. The suture retainer of claim 1 wherein the suture-engaging tabs possess an approximately W-configuration.

3. The suture retainer of claim 1 wherein the suture-engaging tabs possess an approximately S-configuration.

4. The suture retainer of claim 1 wherein the suture-engaging tabs possess an approximately Z-configuration.

5. The suture retainer of claim 1 wherein the base panel is of rectangular geometry, there are four suture-engaging tabs and each suture-engaging tab occupies a corner region of the base panel.

6. A suture retainer comprising:
   a base panel possessing a plurality of spaced-apart suture-engaging tabs defined thereon,
   each said suture-engaging tab comprising at least one pair of opposing elements, with one element of said pair being elevated above a plane of said base panel and said other element of said pair being depressed below said base panel plane, when said suture retainer is in packaged condition,
   a plurality of spaced-apart needle-engaging tabs defined upon the base panel,
   the number and distribution of the needle-engaging tabs being such as to accommodate a variety of needle sizes or configurations, and
   a surgical needle point-retaining member on the base panel.

7. The suture retainer of claim 6 wherein the surgical needle point-retaining member is a section of polymeric foam.

8. The suture retainer of claim 1 wherein the needle-engaging tabs are asymmetrically distributed upon the base panel in the central region thereof.

9. The suture retainer of claim 5 wherein the needle-engaging tabs are asymmetrically distributed upon the base panel in the central region thereof.

10. The suture retainer of claim 1 wherein the needle-engaging tabs are irregularly distributed upon the base panel in the central region thereof.

11. The suture retainer of claim 5 wherein the needle-engaging tabs are irregularly distributed upon the base panel in the central region thereof.

12. The suture retainer of claim 1 wherein the suture-engaging tabs possess an approximately N- configuration.

13. The suture retainer of claim 5 wherein the base panel is of square geometry.

14. A suture retainer comprising:
 a base panel possessing a plurality of spaced-apart suture-engaging tabs defined thereon,
 each said suture-engaging tab comprising at least one pair of opposing elements, with one element of said pair being elevated above a plane of same base panel, and said other element of said pair being depressed below said base panel plane, when said suture retainer is in packaged condition,
 a plurality of spaced-apart needle-engaging tabs defined upon the base panel,
 the number and distribution of the needle-engaging tab being such as to accommodate a variety of needle sizes or configurations, and
 a cover panel attached to said base panel along a common edge.

15. The suture retainer of claim 14 wherein said common edge constitutes a fold line to facilitate folding over of said cover panel upon said base panel in the packaged condition of said retainer.

16. The suture retainer of claim 15 wherein said cover panel additionally comprises a slit therein and said base panel additionally comprises a slit therein, such that said respective slits on said cover panel and base panel can be made to engage one another by twisting action which locks said panels together when said cover panel is folded over said base panel.

17. The suture retainer of claim 14 additionally comprising:
 a second base panel sandwiched between said first base panel and said cover panel when said cover panel is folded over said first base panel.

* * * * *